United States Patent [19]

Shimotori et al.

[11] Patent Number: 5,240,951
[45] Date of Patent: Aug. 31, 1993

[54] ISOTHIAZOLECARBOXYLIC ACID DERIVATIVES, RICE BLAST CONTROL AGENTS CONTAINING THE SAME AS ACTIVE INGREDIENTS, AND RICE BLAST CONTROL METHOD APPLYING THE CONTROL AGENTS

[75] Inventors: Hitoshi Shimotori, Chiba; Yuji Yanase; Takeshi Sekino, both of Mobara; Katsutoshi Ishikawa, Kanagawa; Toshiaki Kuwatsuka, Mobara; Hiroharu Tanikawa, Mobara; Hideo Kawashima, Mobara; Naofumi Tomura, Mobara; Yoshiro Kanemoto, Mobara, all of Japan

[73] Assignee: Mitsui Toatsu Chemicals, Incorporated, Tokyo, Japan

[21] Appl. No.: 761,217

[22] Filed: Sep. 19, 1991

[30] Foreign Application Priority Data

Sep. 20, 1990 [JP] Japan .................. 2-248623
May 28, 1991 [JP] Japan .................. 3-123454
Jun. 24, 1991 [JP] Japan .................. 3-151312

[51] Int. Cl.⁵ ............... A01N 43/80; A01N 43/84; C07D 275/03
[52] U.S. Cl. .................. 514/372; 514/236.8; 548/213; 548/214
[58] Field of Search ............. 544/133; 548/213, 214; 514/236.8, 372

[56] References Cited

U.S. PATENT DOCUMENTS 3,341,547  9/1967  Mailey ...................... 548/214
3,403,209  9/1968  Bushong et al. .......... 548/214

FOREIGN PATENT DOCUMENTS 0302183  2/1989  European Pat. Off. .

Primary Examiner—Joseph Paul Brust
Assistant Examiner—Mary Susan H. Gabilan
Attorney, Agent, or Firm—Millen, White, Zelano & Branigan

[57] ABSTRACT

Application of a rice blast control agent containing an isothiazolecarboxylic acid derivative of the below-described formula, which shows excellent activity against rice blast (*Pyricularia oryzae*) in rice cultivation, to the water surface of a paddy rice field results in the absorption of the derivative through roots of rice plants, so that the resistance of the rice plants can be enhanced.

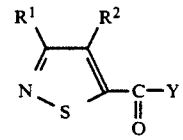

wherein $R^1$ and $R^2$ independently mean a hydrogen or halogen atom or a particular group, and Y stands for an $OR_3$ group ($R^3$ being a hydrogen or alkali metal atom or a particular group), an $NHR^4$ group ($R^4$ being a hydrogen atom or a particular group), or a morpholino group.

10 Claims, No Drawings

ISOTHIAZOLECARBOXYLIC ACID DERIVATIVES, RICE BLAST CONTROL AGENTS CONTAINING THE SAME AS ACTIVE INGREDIENTS, AND RICE BLAST CONTROL METHOD APPLYING THE CONTROL AGENTS

BACKGROUND OF THE INVENTION

1) Field of the Invention

This invention relates to isothiazolecarboxylic acid derivatives showing excellent activity against rice blast (*Pyricularia oryzae*) in rice cultivation, rice blast control agents containing the same as active ingredients, and rice blast control methods applying the control agents.

2) Description of the Related Art

Control of disease and insect damage plays an important role in the cultivation of rice. Rice blast (*Pyricularia oryzae*) is a particularly serious disease so that a variety of fungicides and control methods have been developed and utilized. These control methods or fungicides are, however, not believed to be fully effective. Indeed, they involve one or more drawbacks still to be overcome, such as the control effects. Certain isothiazolecarboxylic acid derivatives are disclosed to have fungicidal and bactericidal activity in Japanese Patent Publication No. 1995/1968, in which it is described that isothiazole carboxylic acid esters and amine salts show control effects on the tomato disease caused by *Xanthomonas vesicatoria*, the soybean disease triggered by *Uromyces phaseoli* var. typica and tobacco wildfire. However, this patent publication makes no mention of their effects on rice blast.

Further, U.S. Pat. No. 3,341,547 (1967) discloses that isothiazolecarboamides have herbicidal effects.

Specific effects for a particular disease, however, cannot be generalized by assuming their effectiveness for other diseases. It has also been demonstrated by known facts or empirical rules that herbicidal effects and the control of a particular disease cannot be discussed in a similar manner. For example, agricultural streptomycin is used against tobacco wildfire and the plant disease caused by Xanthomonas but exhibits absolutely no effects on rice blast. Conversely, isoprothiolane, pyrochelon and the like, which are widely used as rice blast control agents, do not show any effects on other diseases.

Rice blast is a disease which causes severe damage in the paddy field. Various control methods have therefore been attempted to date. Several kinds of chemicals are used these days as fungicides for the control of rice blast. However, they are however insufficient in many aspects such as fungicidal effects.

In general, the effectiveness or ineffectiveness of a fungicide can be tested in vitro. It is easy to investigate the fungicide in an experimental room. This is attributed to the fact that the fungicide acts directly on the corresponding fungus. However, some chemicals which have no fungicidal effects in vitro can control plant diseases. Such indirect effects, however, cannot be tested in vitro in many instance, so that it is not easy to study them.

SUMMARY OF THE INVENTION

With a view toward overcoming the above-described problems of the conventional control agents, the present inventors have proceeded with an investigation about possible control effects of various compounds on rice blast. As a result, it has been found that certain specific isothiazolecarboxylic acid derivatives have excellent control effects on rice blast, leading to the completion of the present invention.

They have the unique property that, although these derivatives themselves do not exhibit significant antifungal activities against *Pyricularia oryzae*, they act on the rice, thus enhancing resistance to rice blast.

The present invention therefore provides a rice blast control agent comprising, as an active ingredient, an isothiazolecarboxylic acid derivative represented by the following formula (I):

wherein $R^1$ means a hydrogen or halogen atom or a $C_{1-4}$ alkyl or $C_{1-3}$ alkoxyl group, $R^2$ denotes a hydrogen or halogen atom or a nitro or $C_{1-4}$ alkyl group, and Y stands for an $OR_3$ group ($R^3$ being a hydrogen or alkali metal atom, a $C_{1-4}$ alkyl group or an $NHR^5R^6R^7$ group, $R^5$, $R^6$ and $R^7$ being a hydrogen atom or a $C_{1-4}$ alkyl group), an $NHR^4$ group ($R^4$ being a hydrogen atom, a linear or branched $C_{1-16}$ alkyl, $C_{5-7}$ cycloalkyl, cyclohexenyl, dimethylamino or furfuryl group, or a $C_{1-4}$ alkyl group substituted by one or more $C_{1-8}$ alkoxyl, $C_{1-3}$ alkylthio, phenyl and/or halogenophenyl groups), or a morpholino group, a preparation process of the derivative, a rice blast control agent containing the derivative as an active ingredient, and a rice blast control method applying the control agent.

When a paddy rice field is treated with the control agent by submerged application, the derivative is absorbed in the rice plant so that resistance can be enhanced significantly.

Although some of the isothiazolecarboxylic acid derivatives embraced by the above formula (I) are compounds known to the public, their amide derivatives are novel compounds. None of the compounds have heretofore been known to have control effects on rice blast on any practical level.

DETAILED DESCRIPTION OF THE INVENTION

The compounds of the present invention have extremely unique effects in that they show excellent control effects on rice blast although they do not have substantial antifungal effects for *Pyricularia oryzae* or, even if any, their antifungal effects are extremely weak. Application of any rice blast control agent according to the present invention to rice plants is believed to promote the production of an antifungal substance such as phytoalexin within the bodies of the rice plants, gives resistance to damage caused by disease, prevents infection to *Pyricularia oryzae* and avoids the development of the disease. Such unique effects cannot be found by any antimicrobial test which has been commonly conducted to date, such as a Petri dish test.

Examples of Japanese Patent Publication No. 1995/1968 describe that isothiazolecarboxylic acid esters show control effects on the tomato disease caused by *Xanthomonas vesicatoria*, the soybean disease triggered by *Uromyces phase oli* var. typica and tobacco wildfire and have antifungal effects for several varieties of fungi such as *Aspergillus niger, Penicillium expansum* and *Alternaria solani.*

Rice blast for which the derivatives of the present invention have now been found effective is totally different from the diseases mentioned above and is a disease by which rice is infected. Even in view of examples in the past, it is quite clear that chemicals effective on the above disease cannot be inferred at all from the chemicals effective on other diseases. For example, agricultural streptomycin is used for tobacco wildfire or the disease causes by Xanthomonas but does not shows no effects whatsoever or *Pyricularia oryzae.* Conversely, isoprothiolane, pyroguilon and the like, which are widely used as rice blast control agents, do not show any effects for other diseases.

Among the compounds represented by the formula (I), those capable of showing more preferred rice blast control effects are isothiazolecarboxylic acid derivatives in which Y is represented by $OR^3$, $R^3$ being a hydrogen or alkali metal atom, or by $NHR^4$, $R^4$ being a hydrogen atom or a linear or branched $C_{1-16}$ alkyl group. Rice blast control agents containing them as active ingredients are more effective.

Although some of the compounds embraced by the formula (I) are compounds known to date, the isothiazolecarboxylic acid amide derivatives represented by the following formula (II) are novel compounds.

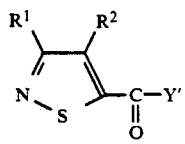

wherein $R^1$ means a hydrogen or halogen atom or a $C_{1-4}$ alkyl or $C_{1-3}$ alkoxyl group, $R^2$ denotes a hydrogen or halogen atom or a nitro or $C_{1-4}$ alkyl group, and $Y'$ stands for an $NHR^4$ group ($R^4$ being a linear or branched $C_{4-16}$ alkyl, $C_{5-7}$ cycloalkyl, cyclohexenyl, dimethylamino or furfuryl group, or a $C_{1-4}$ alkyl group substituted by one or more $C_{1-8}$ alkoxyl, $C_{1-3}$ alkylthio, phenyl and/or halogenophenyl groups), or a morpholino group.

Novel compounds capable of exhibiting more preferred rice blast control effects can include isothiazole carboxylic amide derivatives of the formula (II) in which $Y'$ represents an $NHR^4$ group, $R^4$ being a hydrogen atom or a linear or branched $C_{4-16}$ alkyl group.

The compounds represented by the formula (II) can be prepared in a manner described in Japanese Patent publication Nos. 1995/1968 and 21432/1968, following the route indicated below by Reaction Formulas 1, 2 and 3.

Reaction scheme 1

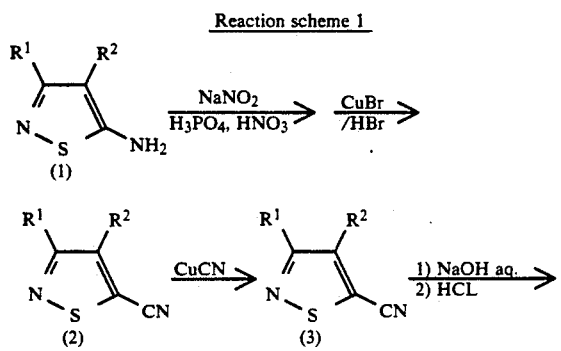

-continued
Reaction scheme 1

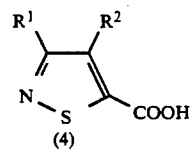

Reaction scheme 2

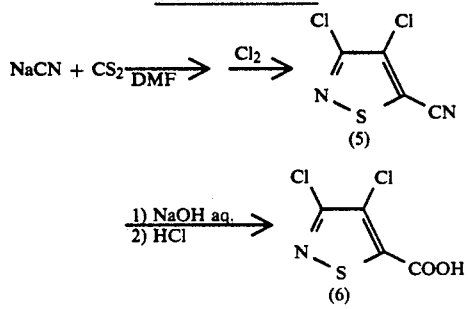

Reaction scheme 3

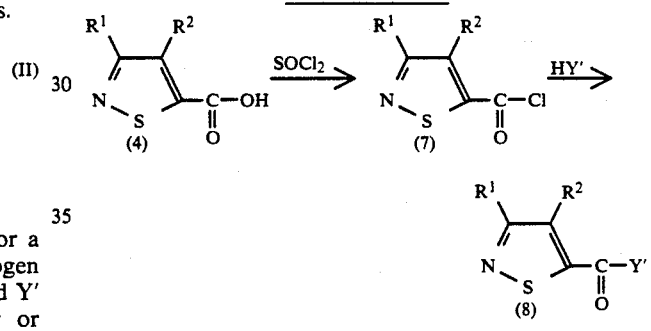

The compounds of the formula (I), which are not embraced by the formula (II), are the known compounds. Where Y stands for an $-O^-\,{}^+NHR^5R^6R^7$ group, these compounds can be prepared based on the following reaction scheme 4:

Reaction Scheme 4

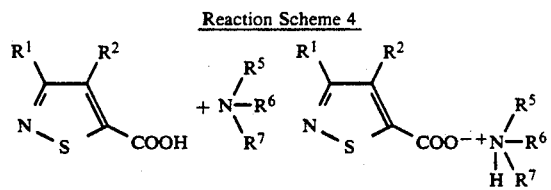

The reactions represented by Reaction scheme 3, which pertain to the preparation of the novel compounds of the present invention, will be described next in detail.

An isothiazole-5-carboxylic acid derivative (4) is converted with thionyl chloride to a carboxylic acid chloride (7) by a method know per se in the art. Although the reaction proceeds smoothly even when the isothiazole-5-carboxylic acid derivative (4) and thionyl chloride are simply mixed and heated, the reaction may be carried out in benzene, toluene or other inert solvent. After they are reacted under reflux for about 1–3 hours, excess thionyl chloride is distilled out. Addition of a solvent such as benzene or toluene and subsequent distillation permit complete removal of thionyl chloride. The residue can be used as the carboxylic acid chloride in the subsequent step.

The acid chloride (7) so obtained is next reacted with one of various amines, whereby an isothiazole-5-carboxylic acid amide derivative (8) can be obtained. Usual amide synthesis processes can all be applied to this amidation. A description will hereinafter be made of a representative process. The acid chloride is dissolved in an inert solvent such as benzene, toluene, xylene, tetrahydrofuran, dioxane, ethyl acetate, chloroform or dimethylformamide, to which a base such as triethylamine or pyridine is added in an amount equivalent to or in slight excess of the carboxylic acid chloride (7). The resultant mixture is cooled over an ice-water bath, and the amine is gradually added at 5°–10° C. Although the reaction proceeds instantaneously in many instances, the reaction mixture is stirred for additional 30 minutes to 1 hour at the same temperature to bring the reaction to completion. The reaction can be conducted using the amine in an amount of 2 equivalents or more instead of a base such as triethylamine or pyridine.

After completion of the reaction, a large volume of water is added, followed by the addition of a solvent such as ethyl acetate, benzene or toluene for extraction. An organic solvent is washed successively with hydrochloric acid, an aqueous solution of sodium hydrogencarbonate and water, and is then dried over sodium sulfate. Upon distillation of the solvent, the isothiazole-5-carboxylic acid amide derivative (8) is obtained as a pure product. A high-purity product can be obtained by recrystallization or column chromatography, if necessary.

A preparation process of the isothiazolecarboxylic acid amide derivatives represented by the formula (II) can be summarized as follows:

A process for the preparation of an isothiazolecarboxylic acid amide derivative represented by the following formula (II):

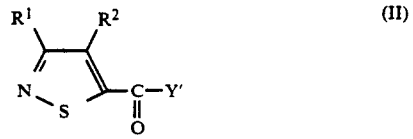

(II)

wherein $R^1$ means a hydrogen or halogen atom or a $C_{1-4}$ alkyl or $C_{1-3}$ alkoxyl group, $R^2$ denotes a hydrogen or halogen atom or a nitro or $C_{1-4}$ alkyl group, and Y' stands for an $NHR^4$ group ($R^4$ being a hydrogen atom, a linear or branched $C_{4-16}$ alkyl, $C_{5-7}$ cycloalkyl, cyclohexenyl, dimethylamino or furfuryl group, or a $C_{1-4}$ alkyl group substituted by one or more $C_{1-8}$ alkoxyl, $C_{1-3}$ alkylthio, phenyl and/or halogenophenyl groups), or a morpholino group, which comprises reacting an acid chloride represented by the following formula (III):

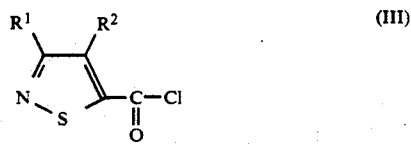

(III)

wherein $R^1$ and $R^2$ have the same meanings as defined above, with an amine represented by the following formula (IV):

$$R^4NH_2 \qquad (IV)$$

wherein $R^4$ represents a hydrogen atom, a linear or branched $C_{4-16}$ alkyl, $C_{5-7}$ cycloalkyl, cyclohexenyl, dimethylamino or furfuryl group, or a $C_{1-4}$ alkyl group substituted by one or more $C_{1-8}$ alkoxyl, $C_{1-3}$ alkylthio, phenyl and/or halogenophenyl groups), or with morpholine.

The agricultural fungicides according to the present invention can be formulated into mixed preparations together with agricultural chemicals such as other fungicides, insecticides, herbicides and plant growth regulators, soil improvers or fertilizing substances, to say nothing of combined use with them.

Although the compounds according to the present invention can be used neat, it is preferable to apply them in the form of compositions mixed with carriers including solid or liquid extenders. The term "carriers" as used herein means synthetic or natural, inorganic or organic materials, which are added to enhance the characteristic feature of the control agents of the present invention, namely, to facilitate the absorption of the derivatives through rice plant roots, thereby imparting resistance to the rice plants upon submerged application and also to facilitate the storage, transportation and handling of the compounds as active ingredients.

Suitable solid carriers include, for example, clays such as montmorillonite, kaolinite and bentonite; inorganic materials such as diatomaceous earth, terra abla, talc, vermiculite, gypsum, calcium carbonate, silica gel and ammonium sulfate; vegetable organic materials such as soybean meal, sawdust and wheat flour; and urea.

Appropriate liquid carriers include, for example, aromatic hydrocarbons such as toluene, xylene and cumene; paraffinic hydrocarbons such as kerosine and mineral oil; halogenated hydrocarbons such as carbon tetrachloride, chloroform and dichloroethane; ketones such as acetone and methyl ethyl ketone; ethers such as dioxane, tetrahydrofuran and diethylene glycol dimethyl ether; alcohols such as methanol, ethanol, propanol and ethylene glycol; dimethylformamide; dimethylsulfoxide; and water.

Further, to enhance the effects of the compounds of the present invention, adjuvants such as those to be described below can be used either singly or in combination depending upon the purpose, in view of the preparation form, the field to be applied, etc.

For emulsification, dispersion, spreading, wetting, binding or stabilization, the following adjuvants can be added: anionic surfactants such as lignine sulfonate salts, alkylbenzene sulfonate salts, alkyl sulfate salts, polyoxyalkylene alkylsulfate salts and polyoxyalkylene alkylphosphate esters; nonionic surfactants such as polyoxyalkylene alkylethers, polyoxyalkylene alkylaryl ethers, polyoxyalkylene alkylamines, polyoxyalkylene alkylamides, polyoxyalkylene alkylthioethers, polyoxyalkylene fatty acid esters, glycerin fatty acid esters, sorbitan fatty acid esters, polyoxyalkylene sorbitan fatty acid esters and polyoxypropylene-polyoxyethylene block polymers; lubricants such as calcium stearate and wax; stabilizers such as isopropylhydrogen phosphate; methylcellulose; carboxymethylcellulose; casein; gum arabic; etc. It is to be noted that adjuvants are not limited to those exemplified above.

The effective amount of each compound of the present invention is generally 0.5-20 wt. % in dust preparations, 5-50 wt. % in emulsions, 9-90 wt. % in wettable powders, 0.1-20 wt. % in granular preparations, and 9-90 wt. % in flowable preparations. On the other hand, the amount of a carrier in individual preparations is generally 60-99 wt. % in dust preparations, 9-90 wt. % in wettable powders, 80-99 wt. % in granular preparations, 40-95 wt. % in emulsions, and 9-90 wt. % in flowable preparations. Further, the total amount of adjuvants is generally 0.1-20 wt. % in dust preparations, 1-20 wt. % in emulsions, 0.1-20 wt. % in wettable powders, 0.1-20 wt. % in granular preparations, and 0.1-20 wt. % in flowable preparations.

The rice blast control agents according to the present invention can be used and can exhibit superb control effects throughout the growth stage in which there is a potential danger of occurrence of *Pyricularia oryzae* in the cultivation of rice.

When they are applied, for example, to a nursery bed in the pre-transplanting rearing stage in usual cultivation, they can show their effects at an application rate of 4–80 g per box (60 cm×30 cm) or, in terms of the amount of the active ingredients, of 0.2–2 g a.i./box. When they are applied to a paddy field subsequent to transplanting, they can be used over the wide range of from immediately after the transplanting to the booting stage and they can exhibit their effects at an application rate of 0.5–5 kg per 10 ares or, in terms of the amount of the active ingredients, of 25–250 g/10 ares.

Similar treatment can of course be used in cultivation methods which do not involve transplanting, such as direct sowing cultivation.

By such an application method, it is possible to promote the production of an antifungal substance, which acts against *Pyricularia oryzae*, within rice plants and hence to enhance resistance to the disease injury.

It therefore takes some time until the control effects of each control agent of this invention are exhibited after its application, because the control agent does not act directly on *Pyricularia oryzae* but does enhance the resistance of rice itself. It is hence desirable to apply the control agent 2–50 days before the time around which rice blast is expected to take place. Although the control agent retains its effects for a period much longer compared to those used to date, the frequency of application may be 1–3 times per season.

Preparation processes of some isothiazolecarboxylic acid derivatives of the formula (I) according to the present invention will next be described by the following examples.

EXAMPLE 1

Synthesis of 3-methyl-5-isothiazolecarboxylic acid (Compound No. 1)

5-Cyano-3-methyl-isothiazole (10.5 g) was heated under reflux for 2 hours in 100 ml of a 2N aqueous solution of sodium hydroxide. A homogeneous solution so formed was cooled down to room temperature and was then ice-cooled. Its pH was thereafter adjusted to pH 3-4 with concentrated hydrochloric acid. Precipitated crystals were collected by filtration and then dried at 60° C. under reduced pressure, whereby 10.1 g of 3-methyl-5-isothiazolecarboxylic acid were obtained (yield: 83.4%). m.p. 203°–204° C.

EXAMPLE 2

Synthesis of 3,4-dichloro-5-isothiazolecarboxylic acid (Compound No. 2)

1) Synthesis of 5-cyano-3,4-dichloroisothiazole

Sodium cyanide (49.0 g) was added to 500 ml of dimethylformamide, followed by the dropwise addition of 76.1 g of carbon disulfide under stirring at room temperature over 1 hour. Heat was generated so that the temperature of the reaction mixture reached 30° C. After completion of the dropwise addition, the mixture was stirred for 1 hour at room temperature and for additional 3 hours at 60° C. The reaction mixture was then allowed to stand for 12 hours at room temperature, during which a great deal of crystals was allowed to precipitate. The crystals so formed were dispersed under stirring in the reaction mixture, and chlorine gas was sparged into the reaction mixture. When the internal temperature reached 70° C. due to the initial exotherm, the reaction mixture was cooled over a water bath. The water bath was removed when the internal temperature dropped to 65° C. This operation was conducted for 2.5 hours while the amount of chlorine gas sparged was adjusted to keep the internal temperatures at 60°–65° C. The reaction was allowed to continue further for 30 minutes until the exotherm subsided and the internal temperature dropped to 35° C. Nitrogen gas was then sparged for 1 hour at room temperature so that remaining chlorine gas was purged out.

When the reaction mixture was added dropwise into 1500 ml of water under vigorous agitation, crystals precipitated with exotherm and foaming. Here, cooling was effected to maintain the water temperature within the range of 35°–60° C. After completion of the dropwise addition, the resultant mixture was stirred under icecooling until the temperature of the mixture dropped to 5° C. A precipitate so formed was then collected by filtration and dissolved in 500 ml of ethyl acetate. After insoluble matter was filtered off, the filtrate was dried over anhydrous magnesium sulfate. When the solvent was distilled off under reduced pressure, plate crystals of an orange color were obtained. The crystals were recrystallized from a least amount of methanol, whereby 5-cyano-3,4-dichloroisothiazole was obtained in a yield of 87.6%. m.p. 84.5°–85° C.

2) Synthesis of 3,4-dichloro-5-isothiazolecarboxylic acid

In 400 ml of a 2N aqueous solution of sodium hydroxide, 19.6 g of 5-cyano-3,4-dichloroisothiazole obtained in Example 2-1) were heated under reflux for 2 hours. The reaction mixture was cooled to 5° C., followed by the addition of concentrated hydrochloric acid to adjust the pH of the reaction mixture to 3-4. Crystals thus precipitated were collected by filtration and recrystallized from boiling water, whereby 18.8 g of white crystals (m.p. 178°–179° C.) were obtained (yield: 86.5%).

IR spectrum ($cm^{-1}$, neat): 2982–2751, 2754, 1733, 1513, 1502, 1419, 1377, 1344, 1315, 1225, 1111, 968, 856, 823, 702.

| Elemental analysis: | C | H | N | Cl | S |
|---|---|---|---|---|---|
| Calculated (%) | 24.36 | 0.51 | 7.07 | 35.81 | 16.16 |
| Found (%) | 23.38 | 0.59 | 7.49 | 34.95 | 16.06 |

The elemental analysis and IR spectrum showed that white crystals were 3,4-dichloro-5-isothiazolecarboxylic acid.

EXAMPLE 3

Synthesis of N-n-butyl-3-methyl-5-isothiazolecarboxylic acid amide (Compound 19)

3-Methyl-5-isothiazolecarboxylic acid (2.3 g) was dissolved in 40 ml of ethyl acetate. After 2 g of triethylamine were added, the resultant mixture was cooled over an ice-water bath and, at 5°–10° C., 1.5 g of n-butylamine were gradually added dropwise. After completion of the dropwise addition, stirring was continued for 30 minutes. The reaction mixture was washed successively with an aqueous solution of sodium hydrogencarbonate and then with water. After dried over sodium sulfate, the solvent was distilled off so that 2.60 g of N-n-butyl-3-methyl-5-isothiazolecarboxylic acid amide were obtained as an oil.

EXAMPLE 4

Synthesis of 3,4-dichloro-N-n-pentyl-5-isothiazolecarboxylic acid amide (Compound No. 29)

Thionyl chloride (6 ml) was added to 0.60 g of 3,4-dichloro-5-isothiazolecarboxylic acid, followed by reflux for 30 minutes. After excess thionyl chloride was distilled off, benzene was added and low-boiling substances were distilled off under reduced pressure. Tetrahydrofuran (15 ml) and triethylamine (0.5 g) were added to the residue, followed by the dropwise addition of a solution of 0.38 g of n-pentylamine in tetrahydrofuran at 5°–10° C. under ice cooling. After the resultant mixture was stirred for 30 minutes at room temperature, the mixture was poured into a large volume of water. An aqueous solution so prepared was then extracted with 100 ml of ethyl acetate, followed by similar processing to Synthesis Example 3. 3,4-Dichloro-N-n-pentyl-5-isothiazolecarboxylic acid amide was obtained as an oil (yield: 0.75 g).

Preparation processes of esters, alkali metal salts and amine salts will be describe hereinafter.

EXAMPLE 5

Synthesis of isopropyl 3,4-dicloroisothiazole-5-carboxylate (Compound No. 6)

Thionyl chloride (20 g) was added to 1.5 g of 3,4-dichloroisothiazole-5-carboxylic acid and the resultant mixture was heated under reflux for 1 hour. After excess thionyl chloride was distilled off under reduced pressure, a small amount of benzene was added, and the solvent was again distilled off under reduced pressure to remove a trace amount of thionyl chloride. Dry diethyl ether (10 ml) was added to the residue, whereby an acid chloride solution was obtained.

2-Propanol (0.54 g) and triethylamine (0.92 g) were dissolved in dry diethyl ether, to which the above-prepared acid chloride solution was added dropwise under ice cooling. They were then reacted at 30° C. for 30 minutes and, after insoluble matter was filtered off, the filtrate was concentrated and then purified by chromatography on a silica gel column (n-hexane:ethyl acetate=9:1) to obtain 1.02 g of the title compound.

EXAMPLE 6

Synthesis of potassium 3,4-dichloroisothiazole-5-carboxylate (Compound No. 7)

Potassium hydroxide (0.27 g) dissolved in 3 ml of water was added to a solution of 3,4-dichloroisothiazole-5-carboxylic acid (0.95 g) in 4 ml of ethanol. The solvent was distilled off under reduced pressure. The crystals thus obtained were washed with a small quantity of ethanol.

EXAMPLE 7

Synthesis of 3,4-dichloro-5-isothiazolecarboxylic acid amide (Compound No. 4)

Concentrated sulfuric acid (10 ml) was added to 1.0 g of 5-cyano-3,4-dichloroisothiazole. When heated at 110° C. for 20 minutes, the isothiazole compound was dissolved completely. The reaction mixture was cooled under ice cooling, and precipitated crystals were collected by filtration. The crystals were then recrystallized from a 1:1 mixed solvent of ethanol and water.

EXAMPLE 8

Synthesis of triethylammonium 3-methylisothiazolecarboxylate (Compound No. 8)

3-Methyl-5-isothiazolecarboxylic acid (1.0 g) was dissolved in 10 ml of dry tetrahydrofuran, to which a solution of 0.72 g of triethylamine in 5 ml of dry tetrahydrofuran were added dropwise under stirring at room temperature. After the resulting mixture was stirred further for 30 minutes at room temperature, the solvent was distilled off under reduced pressure so that 1.71 g (stoichiometric amount) of the title compound were obtained.

EXAMPLE 9

Synthesis of isopropylammonium 3-methyl-5-isothiazolecarboxylate (Compound No. 9)

3-Methyl-5-isothiazolecarboxylic acid (1.0 g) was dissolved in 10 ml of dry tetrahydrofuran, in which a solution of 0.41 g of isopropylamine in 5 ml of dry tetrahydrofuran were added dropwise at room temperature under stirring. White crystals were formed concurrently with the dropwise addition. After the reaction mixture was stirred further at room temperature for 30 minutes, crystals were collected by filtration and washed with a small amount of dry tetrahydrofuran. The crystals were dried at 40° C. for 3 hours under reduced pressure, whereby 1.20 g of the title compound were obtained (yield: 85%).

EXAMPLE 10

Synthesis of triethylammonium 3,4-dichloro-5-isothiazolecarboxylate (Compound No. 10)

In 10 ml of dry tetrahydrofuran, 1.0 g of the 3,4-dichloro-5-isothiazolecarboxylic acid obtained in Example 2 was dissolved, followed by the dropwise addition of a solution of 0.52 g of triethylamine in 5 ml of dry tetrahydrofuran. After the resulting mixture was stirred further at room temperature for 30 minutes, the solvent was distilled off under reduced pressure so that 1.51 g (stoichiometric amount) of the title compound were obtained.

EXAMPLE 11

Synthesis of isopropylammonium 3,4-dichloro-5-isothiazolecarboxylate (Compound No. 11)

In 10 ml of dry tetrahydrofuran, 1.0 g of the 3,4-dichloro-5-isothiazolecarboxylic acid obtained in Example 2 was dissolved. While the resultant mixture was stirred at room temperature, a solution of 0.30 g of isopropylamine in 5 ml of dry tetrahydrofuran was added dropwise. White crystals were formed concurrently with the dropwise addition. After the resulting mixture was stirred further at room temperature for 30 minutes, the crystals were collected by filtration and then washed with a small amount of dry tetrahydrofuran. The crystals were dried at 40° C. for 30 minutes under reduced pressure, whereby 1.10 g of the title compound were obtained (yield: 85%).

Based on the examples described above, other compounds according to the present invention can be easily synthesized by applying the known technology. Representative compounds, including the compounds of the above examples, are shown in Table 1.

TABLE 1

| Comp'd No. | $R^2$ | $R^2$ | Y | m.p. °C. | Physical data |
|---|---|---|---|---|---|
| 1 | Me | H | OH | 203–204 | — |
| 2 | Cl | Cl | OH | 179–179.5 | IR(KBr, cm$^{-1}$) 2982–2751, 2754, 1733, 1513, 1502, 1419, 1377, 1344, 1315, 1225, 1111, 968, 856, 823, 702. |
| 3 | Cl | Cl | NHEt | 77.5–78.5 | NMR 1.23(3H, t, J=7.4Hz), 3.50(2H, m), 5.62(1H, bs.) |
| 4 | Cl | Cl | NH$_2$ | 158.5–160.0 | NMR 5.77(2H, s). |
| 5 | Cl | Cl | OK | 83–84 | — |
| 6 | Cl | Cl | OPr$^{iso}$ | Oil | NMR 1.39(6H, d, J=7.0Hz), 5.02(1H, m). |
| 7 | Cl | Cl | OK | 83.0–85.0 | IR(KBr, cm$^{-1}$) 2840, 2560, 1605, 1390, 1100, 960. |
| 8 | CH$_3$ | H | OHN(Et)$_3^+$ | Oil | IR(KBr, cm$^{-1}$) 2483, 1605, 1402. |
| 9 | CH$_3$ | H | OHNH$_2$Pr$^{iso+}$ | 98–105 | IR(KBr, cm$^{-1}$) 2982, 1577, 1406. |
| 10 | Cl | Cl | OHN(Et)$_3^+$ | Oil | IR(KBr, cm$^{-1}$) 2503, 1605, 1401. |
| 11 | Cl | Cl | OHNH$_2$Pr$^{iso+}$ | 164–165 | IR(KBR, cm$^{-1}$) 2650, 1607, 1405. |
| 12 | CH$_3$ | Cl | OH | 193–195 | |
| 13 | H | Cl | OH | 167–168 | |
| 14 | H | Br | OH | 180–181 | |
| 15 | EtO | Br | OH | | |
| 16 | CH$_3$ | Br | OH | 202–103 | |
| 17 | CH$_3$ | NO$_2$ | OH | 120 | |
| 18 | CH$_3$ | I | OH | 196–198 | |
| 19 | Me | H | —NHC$_4$H$_9$(n) | Oil | NMR 0.96(3H, t, J=7.3Hz), 1.39(1H, q, J=7.4Hz), 1.58(2H, s), 2.52(3H, s), 3.41–3.46(2H, m), 5.94(1H, br), 7.26(1H, s). |
| 20 | Me | H | —NHC$_5$H$_{11}$(n) | Oil | NMR 0.91(3H, t, J=7.3Hz), 1.33–1.36(4H, m), 1.59–1.64(2H, m), 2.52(3H, s), 3.40–3.42(2H, m), 6.04(1H, s), 7.27(1H, s). |
| 21 | Me | H | —NHC$_6$H$_{13}$(n) | Oil | NMR 0.88(3H, t, J=6.6Hz), 1.28–1.35(6H, m), 1.56–1.69(2H, m), 2.51(3H, s), 3.39–3.44(2H, m), 6.07(1H, bs), 7.26(1H, s). |
| 22 | Me | H | —NHC$_7$H$_{15}$(n) | Oil | NMR 0.88(3H, t, J=7.4Hz), 1.26–1.39(8H, m), 1.56–1.59(2H, m), 2.50(3H, s), 3.38–3.43(2H, m), 6.07(1H, bs), 7.27(1H, s). |
| 23 | Me | H | —NHC$_8$H$_{17}$(n) | Oil | NMR 0.88(3H, t, J=7.3Hz) 1.24–1.38(12H, m), 2.49(3H, s), 3.39–3.42(2H, m), 6.02(1H, bs), 7.26(1H, s). |
| 24 | Me | H | —NH-cyclohexyl | 143.7–145.5 | NMR 1.24(2H, m), 1.40(2H, m), 1.67(2H, m), |

TABLE 1-continued

| Comp'd No. | Substituents R² | R² | Y | m.p. °C. | Physical data |
|---|---|---|---|---|---|
| 25 | Me | H | —NH-benzyl | 87.5–89.6 | 1.75(2H, m), 2.02(2H, m), 2.51(3H, s), 3.93(1H, m), 5.79(1H, bs), 7.26(1H, s). NMR 2.51(3H, s), 4.61(2H, d, J=5.8Hz), 6.24(1H, bs), 7.31–7.39(6H, m). |
| 26 | Me | H | —NH-(3-CF₃-benzyl) | Oil | NMR 2.52(3H, s), 4.68(2H, d, J=5.8Hz), 6.38(1H, bs), 7.31(1H, s), 7.48–7.58(4H, m). |
| 27 | Me | H | —NH-(2-phenethyl) | 93.7–94.6 | NMR 2.48(3H, s), 2.94(2H, t, J=6.6Hz), 5.96(1H, bs), 7.17–7.36(5H, m). |
| 28 | Cl | Cl | —NHC₄H₃ | 51.0–55.3 | NMR 0.98(3H, t, J=8.1Hz), 1.24(2H, m), 1.53(2H, m), 3.36(2H, m), 6.83(1H, broad). |
| 29 | Cl | Cl | —NHC₅H₁₁ | Oil | NMR 0.93(3H, t, J=7.4Hz), 1.38(4H, m), 1.66(2H, m), 3.48(2H, m), 6.91(1H, broad). |
| 30 | Cl | Cl | —NHC₆H₁₃ | Oil | NMR 0.90(3H, t, J=6.6Hz), 1.24–1.43(4H, m), 1.64(2H, m), 3.48(2H, m), 4.11(2H, m) 6.91(1H, broad). |
| 31 | Cl | Cl | —NHC₇H₁₅ | Oil | NMR 0.89(3H, t, J=6.6Hz), 1.24–1.41(8H, m), 1.65(2H, m), 3.47(2H, m), 6.88(1H, broad). |
| 32 | Cl | Cl | —NHC₈H₁₇ | Oil | NMR 0.88(3H, t, J=7.4Hz), 1.28–1.39(10H, m), 1.65(2H, m), 3.48(2H, m), 6.89(1H, broad). |
| 33 | Cl | Cl | —NH-cyclohexyl | 146–148 | NMR 1.23–2.04(10H, m), 3.99(1H, m), 6.72(1H, broad). |
| 34 | Cl | Cl | —NH-furfuryl | 53.5–55.0 | NMR 4.60(2H, d, J=5.3Hz), 6.10–6.34(3H, m), 6.84(1H, broad). |
| 35 | Cl | Cl | 4-morpholino | Oil | NMR 3.75(broad). |
| 36 | Cl | Cl | —NH-(4-Cl-benzyl) | 62.5–65.6 | NMR 4.64(2H, d, J=5.9Hz), 7.22–7.36(4H, m), 9.34(1H, broad). |
| 37 | CH₃ | H | —NH(CH₂)₃—C₆H₅ | Oil | NMR 1.96(2H, m), 2.49(3H, s), 2.72(2H, t, J=7.3Hz), 3.46(2H, t, J=7.3Hz), 5.94(1H, 6s), 7.09(1H, s), 7.21(3H, m), 7.30(2H, m). |
| 38 | CH₃ | H | —NH(CH₂)₃OCH₂CH(C₂H₅)—C₄H₉(n) | Oil | NMR 0.85–0.89(6H, m), 1.26–1.29(9H, m), 1.87(2H, m), 2.50(3H, s), 3.33(2H, m), 3.55(2H, m), 3.59(2H, m), 7.05(1H, bs), 7.22(1H, s). |
| 39 | CH₃ | H | —NH(CH₂)₃SCH₃ | Oil | NMR 1.91(2H, m), 2.12(3H, s), 2.51(3H, s), 2.60(2H, m), 3.55(2H, m), 6.53(1H, bs), 7.27(1H, s). |
| 40 | CH₃ | H | —NHCH₂CH₂CH(C₂H₅)—C₄H₉(n) | Oil | NMR 0.90–0.94(6H, m), 1.30–1.38(9H, m), 2.51(3H, s), 3.35–3.39(2H, m), 6.00(1H, bs), 7.29(1H, s). |
| 41 | CH₃ | H | —NHC(CH₃)(CH₃)—C₆H₄(p-Cl) | Oil | NMR 1.77(6H, s), 2.51(3H, s), 6.17(1H, bs), 7.25(1H, s), 7.21–73.6(4H, m). |
| 42 | Cl | Cl | —NH(CH₂)₉CH₃ | 42.5–43.0 | NMR 0.88(3H, t, J=7.0Hz), 1.27–1.34(14H, m), 1.64(2H, m), 3.48(2H, m), 6.81(1H, bs). |
| 43 | Cl | Cl | —NH(CH₂)₁₃CH₃ | 55.0–58.0 | NMR 0.88(3H, t, J=7.0Hz), 1.26–1.43(22H, m), 1.63(2H, m), 3.48(2H, m), 6.81(1H, bs). |
| 44 | Cl | Cl | —NH(CH₂)₁₅CH₃ | 66.0–67.5 | NMR 0.88(3H, t, J=7.4Hz), 1.26–1.34(26H, m), 1.64(2H, m), 3.48(2H, m), 6.80(1H, bs). |

TABLE 1-continued

| Comp'd No. | R² | R² | Y | m.p. °C. | Physical data |
|---|---|---|---|---|---|
| 45 | CH₃ | Br | OH | 203.0-204.0 (decom'd) | NMR 2.56(3H, s), 11.28(1H, s). |
| 46 | CH₃ | H | —NHCH₂—C₄H₉ (t) | 135.9-137.0 | NMR 0.94(9H, s), 2.51(3H, s), 3.23(2H, d, J=7Hz), 6.01(1H, br), 7.27(1H, s). |
| 47 | CH₃ | H | —NHCH(CH₃)—C₃H₇(n) | 79.5-81.0 | NMR 0.95(3H, t, J=7Hz), 1.22(3H, d, J=7Hz), 1.39(2H, m), 1.51(2H, m), 2.51(3H, s). |
| 48 | CH₃ | H | —NHCH(CH₃)C₅H₁₁(n) | Oil | NMR 0.86(3H, t, J=7Hz), 1.21(3H, d, J=7Hz), 1.25-1.40(6H, m), 1.50(2H, m), 2.50(3H, s), 4.13(1H, m), 5.86(1H, d, J=7Hz), 7.26(1H, s). |
| 49 | CH₃ | H | —NHCH(C₃H₇(n))₂ | 145.3-145.9 | NMR 0.90(6H, t, J=7Hz), 1.3-1.6(8H, m), 2.52(3H, s), 4.09(1H, m), 5.64(1H, d, J=7Hz), 7.26(1H, s). |
| 50 | CH₃ | H | —NHCH(CH₃)—C₆H₁₃(n) | Oil | NMR 0.85(3H, t, J=7Hz), 1.2-1.4(8H, m), 1.25(3H, d, J=7Hz), 1.5-1.6(2H, m), 2.50(3H, s), 4.08-4.15(1H, m), 5.84(1H, br), 7.23(1H, s). |
| 51 | CH₃ | H | —NH-cycloheptyl | 141.0-141.5 | NMR 1.5-1.8(10H, m), 2.02(2H, m), 4.10(1H, m), 5.90(1H, br), 7.25(1H, s). |
| 52 | CH₃ | H | —NHCH(CH₃)—(CH₂)₃CH(CH₃)₂ | Oil | NMR 1.85(6H, d, J=7Hz), 1.15-1.25(2H, m), 1.23(3H, d, J=7Hz), 1.30-1.40(2H, m), 1.45-1.55(3H, m), 2.51(3H, s), 4.15(1H, m), 5.85(1H, br), 7.27(1H, s). |
| 53 | CH₃ | H | —NHCH₂CH₂-cyclohexenyl | 77.5-79.0 | NMR 1.55-1.65(4H, m), 1.95-2.05(4H, m), 2.25(2H, m), 2.53(3H, s), 3.48(2H, m), 5.52(1H, br), 5.97(1H, br), 7.25(1H, s). |
| 54 | CH₃ | H | —NHN(CH₃)₂ | 161.0-162.5 | NMR 2.51(3H, s), 2.78(6H, s), 7.01(1H, br), 7.75(1H, s). |
| 55 | CH₃ | H | NH(CH₂)₃OC₄H₉(n) | Oil | NMR 0.99(3H, t, J=7Hz), 1.1-1.7(6H, m), 2.51(3H, s), 3.4-3.7(6H, m), 3.70(1H, s), 7.60(1H, br). |

NMR measurement conditions: 400 MHz, δ from TMS, solvent: CDCl₃

Although these compounds can be used neat, but their use in the form of preparations is more effective. Preparation examples will hereinafter be described. It is to be noted that the following preparation examples are given by way of example. All designations of "part" or "parts" in the following examples mean "part or parts by weight" or "wt. %".

PREPARATION EXAMPLE 1 (Granular Preparation)

Five parts of 3-methylisothiazole-5-carboxylic acid (Compound No. 1), 22 parts of bentonite, 70 parts of talc, 3 parts of "Sorpol 5060" (surfactant; trade name of Toho Chemical Industry Co., Ltd.) and a small amount of a defoaming agent were kneaded to a uniform mass, granulated by a basket granulating machine and then dried, so that a granular preparation was obtained.

PREPARATION EXAMPLE 2 (Granular Preparation)

Five parts of 3,4-dichloroisothiazole-5-carboxylic acid (Compound No. 2), 60 parts of bentonite, 31 parts of talc, 1 part of sodium dodecylbenzenesulfonate, 1 part of polyoxyethylene alkylaryl ether and 2 parts of sodium ligninesulfonate were mixed. The mixture was added with a suitable amount of water and kneaded. The resultant mass was granulated by a granulating machine and dried in a manner known per se in the art, so that 100 parts of a granular preparation were obtained.

PREPARATION EXAMPLE 3 (Granular Preparation)

Five parts of 3,4-dichloroisothiazole-5-carboxylic acid amide (Compound No. 4), 35 parts of bentonite, 57 parts of talc, 2 parts of sodium ligninesulfonate and 1 part of sodium dodecylbenzenesulfonate were mixed.

The mixture was added with a suitable amount of water and kneaded. The resultant mass was granulated by a granulating machine and dried in a manner known per se in the art, so that 100 parts of a granular preparation were obtained.

PREPARATION EXAMPLE 4 (Granular Preparation)

Five parts of potassium 3,4-dichloroisothiazole-5-carboxylate (Compound No. 5), 60 parts of bentonite, 31 parts of clay, 2.5 parts of sodium alkylbenzenesulfonate and 0.5 part of polyvinyl alcohol were ground and mixed into a uniform mixture. The mixture was added with a suitable amount of water and kneaded. The resultant mass was granulated by a granulating machine and dried in a manner known per se in the art, so that 100 parts of a granular preparation were obtained.

PREPARATION EXAMPLE 5 (Granular Preparation)

Two parts of 3-methyl-N-n-octylisothiazole-5-carboxylic acid amide (Compound No. 23), 94.7 parts of clay, 0.2 part of dialkyl sulfosuccinate, 0.1 part of sodium alkyl sulfates and 3.0 parts of sodium polycarboxylate were ground and mixed into a uniform mixture. The mixture was added with a suitable amount of water and kneaded. The resultant mass was granulated by a granulating machine and dried in a manner known per se in the art, so that 100 parts of a granular preparation were obtained.

PREPARATION EXAMPLE 6 (Granular Preparation)

Three parts of N-n-heptyl-3-methylisothiazole-5-carboxylic acid amide (Compound No. 22), 93.5 parts of clay, 0.5 part of dialkyl sulfosuccinate and 3 parts of carboxymethylcellulose were ground and mixed into a uniform mixture. The mixture was added with a suitable amount of water and kneaded. The resultant mass was granulated by a granulating machine and dried in a manner known per se in the art, so that 100 parts of a granular preparation were obtained.

PREPARATION EXAMPLE 7 (Wettable Powder)

Fifty parts of N-n-butyl-3-methyl-5-isothiazolecarboxylic acid amide (Compound No. 19), 40 parts of calcium carbonate, 5 parts of "Solpol 5039" (mixture of anionic surfactant and white carbon; trade name of Toho Chemical Industry Co., Ltd.) and 5 parts of white carbon were uniformly mixed and ground into a wettable powder.

PREPARATION EXAMPLE 8 (Wettable Powder)

Seventy parts of N-n-pentyl-3-methyl-5-isothiazolecarboxylic acid amide (Compound No. 20), 25 parts of kaolinite, 3 parts of "Solpol 5039" and 2 parts of white carbon were uniformly mixed and ground into a wettable powder.

PREPARATION EXAMPLE 9 (Wettable Powder)

Fifty parts of N-n-hexyl-3-methyl-5-isothiazolecarboxylic acid amide (Compound No. 21), 40 parts of calcium carbonate, 5 parts of "Solpole 5039" and 5 parts of white carbon were uniformly mixed and ground into a wettable powder.

PREPARATION EXAMPLE 10 (Wettable Powder)

Seventy parts of N-n-heptyl-3-methyl-5-isothiazolecarboxylic acid amide (Compound No. 22), 25 parts of kaolinite, 3 parts of "Solpol 5039" and 2 parts of white carbon were uniformly mixed and ground into a wettable powder.

PREPARATION EXAMPLE 11 (Wettable Powder)

Among forty parts of 3,4-dichloro-N-n-hexyl-5-isothiazolecarboxylic acid amide (Compound No. 30), 5 parts of "Solpol 3353" (nonionic surfactant; trade name of Toho Chemical Industry Co. Ltd.), 5 parts of a 1% aqueous solution of xanthan gum, 40 parts of water and 10 parts of ethylene glycol, the ingredients other than the active ingredient were combined into a uniform solution. The compound of the present invention was then added. After thorough stirring, the mixture was wet-ground in a sand mill so that a wettable powder was obtained.

PREPARATION EXAMPLE 12 (Emulsion)

Twenty parts of 3,4-dichloro-N-n-octyl-5-isothiazolecarboxylic acid amide (Compound No. 32), 55 parts of xylene, 20 parts of N,N-dimethylformamide and 5 parts of "Solpol 2680" (surfactant; trade name of Toho Chemical Industry Co., Ltd.) were uniformed mixed into an emulsion.

PREPARATION EXAMPLE 13 (Flowable Preparation)

Among 40 parts of N-n-heptyl-3-methyl-5-isothiazolecarboxylic acid amide (Compound No. 22), 5 parts of "Solpol 3353", 5 parts of a 1% aqueous solution of xanthan gum, 40 parts of water and 10 parts of ethylene glycol, the ingredients other than the active ingredient were combined into a uniform solution. The compound of the present invention was then added. After thorough stirring, the mixture was wet-ground in a sand mill so that a flowable preparation was obtained.

PREPARATION EXAMPLE 14 (Dust Preparation)

Ten parts of N-n-octyl-3-methyl-5-isothiazolecarboxylic acid amide (Compound No. 23) and 90 parts of clay were uniformly mixed so that a dust preparation was obtained.

PREPARATION EXAMPLE 15 (Dust Preparation)

Five parts of 3,4-dichloro-N-n-heptyl-5-isothiazolecarboxylic acid amide (Compound No. 31), 40 parts of clay and 55 parts of talc were ground and mixed so that a dust preparation was obtained.

Possession of excellent rice blast control effects by the rice blast control agents according to the present invention will next be described specifically by the following tests.

TEST 1 (Rice Blast Control Effect Test—Treatment in Nursery Bed)

In each test, rice seedlings (variety: Mangetsu Mochi; 2-leaf stage) which had been reared in a rice nursery bed (30 cm × 60 cm) were treated at a predetermined application rate per bed with a granular preparation formulated as in Preparation Example 2. Three days later, the rice seedlings were transplanted to 1/5000-are Wagner pots and raised in a greenhouse. Thirty days after the transplanting, a spore suspension of *Pyricularia oryzae* was sprayed and inoculated on the rice plant. The rice plants were then allowed to grow for 1 week at 25° C. under high humidity conditions, and the number of lesions was counted. The control value was calculated in accordance with the following formula. The results of three repetitions are summarized in Table 2.

TABLE 2

Control value (%) =

$$\left(1 - \frac{\text{Number of lesions in treated plot}}{\text{Number of lesions in untreated plot}}\right) \times 100$$

| Compound No. | Control value (%) | |
|---|---|---|
| | 1 g a.i./box | 0.5 g a.i./box |
| 1 | 81 | 79 |
| 2 | 83 | 84 |
| 3 | 66 | 61 |
| 4 | 79 | 72 |
| 5 | 79 | 78 |
| 6 | 69 | 67 |
| 7 | 63 | 61 |
| 8 | 75 | 72 |
| 9 | 63 | 61 |
| 10 | 75 | 72 |
| Control* compound A | 63 | 57 |
| Untreated | 0 | 0 |

*Control compound A: Probenazole [3-allyloxy-1,2-benzoisothiazole-1,1-dioxide]

| | 1 g a.i./box | | 0.5 g a.i./box | |
|---|---|---|---|---|
| Compound No. | Control value (%) | Injury | Control value (%) | Injury |
| 19 | 70 | None | 65 | None |
| 20 | 73 | None | 65 | None |
| 21 | 74 | None | 71 | None |
| 22 | 90 | None | 85 | None |
| 23 | 93 | None | 87 | None |
| 24 | 95 | None | 89 | None |
| 25 | 60 | None | 59 | None |
| 28 | 71 | None | 62 | None |
| 29 | 85 | None | 82 | None |
| 30 | 88 | None | 79 | None |
| 31 | 88 | None | 80 | None |
| 32 | 81 | None | 89 | None |
| 33 | 76 | None | 77 | None |
| 34 | 75 | None | 66 | None |
| 35 | 87 | None | 79 | None |
| 36 | 68 | None | 60 | None |
| Probenazole* | 58 | None | 45 | None |
| Untreated | 0 | — | 0 | — |
| 12 | 85 | None | 80 | None |
| 13 | 80 | None | 74 | None |
| 16 | 84 | None | 82 | None |
| 18 | 89 | None | 84 | None |
| 37 | 85 | None | 76 | None |
| 38 | 87 | None | 76 | None |
| 39 | 87 | None | 59 | None |
| 40 | 77 | None | 77 | None |
| 41 | 79 | None | 56 | None |
| 42 | 79 | None | 56 | None |
| 43 | 90 | None | 85 | None |
| 44 | 86 | None | 80 | None |
| 45 | 85 | None | 82 | None |
| 46 | 88 | None | 85 | None |
| 53 | 77 | None | 65 | None |
| 54 | 80 | None | 75 | None |
| Probenazole* | 65 | None | 57 | None |
| Untreated | 0 | — | 0 | — |

*Control compound

TEST 2 (Rice Blast Control Effect Test—Submerged Application Test)

In each test, rice seedlings (variety: Mangetsu Mochi; 3-leaf stage) were transplanted to 1/10,000—are Wagner pots and then reared for 1 week in a greenhouse. The rice seedlings were treated by applying a granular preparation, which had been formulated as in Preparation Example 2, at a predetermined application rate per are on the water surface. Thirty days after the application, a spore suspension of Pyricularia oryzae was sprayed and inoculated on the foliages of rice plants. The rice plants were then allowed to grow for 1 week at 25° C. under high humidity conditions, and the number of lesions was counted at 1-week intervals. The results of three replications are summarized in Table 3.

TABLE 3

| Compound No. | Control value (%) | |
|---|---|---|
| | 10 g a.i./are | 5 g a.i./are |
| 1 | 82 | 71 |
| 2 | 88 | 88 |
| 3 | 71 | 65 |
| 4 | 82 | 76 |
| 5 | 82 | 82 |
| 6 | 71 | 71 |
| 7 | 75 | 65 |
| 8 | 82 | 76 |
| 9 | 75 | 66 |
| 10 | 82 | 71 |
| Probenazole* | 66 | 59 |
| Untreated | 0 | 0 |

| | 10 g a.i./box | | 5 g a.i./box | |
|---|---|---|---|---|
| Compound No. | Control value (%) | Injury | Control value (%) | Injury |
| 19 | 75 | None | 68 | None |
| 20 | 73 | None | 68 | None |
| 21 | 79 | None | 65 | None |
| 22 | 89 | None | 88 | None |
| 23 | 90 | None | 83 | None |
| 24 | 95 | None | 90 | None |
| 25 | 65 | None | 60 | None |
| 28 | 71 | None | 71 | None |
| 29 | 89 | None | 82 | None |
| 30 | 83 | None | 71 | None |
| 31 | 85 | None | 71 | None |
| 32 | 83 | None | 73 | None |
| 33 | 79 | None | 77 | None |
| 34 | 72 | None | 65 | None |
| 35 | 85 | None | 79 | None |
| 36 | 70 | None | 62 | None |
| Probenazole* | 60 | None | 55 | None |
| Untreated | 0 | — | 0 | — |
| 12 | 87 | None | 80 | None |
| 13 | 83 | None | 83 | None |
| 16 | 85 | None | 85 | None |
| 18 | 86 | None | 80 | None |
| 37 | 90 | None | 83 | None |
| 38 | 92 | None | 86 | None |
| 39 | 90 | None | 80 | None |
| 40 | 81 | None | 73 | None |
| 41 | 85 | None | 70 | None |
| 42 | 83 | None | 75 | None |
| 43 | 93 | None | 90 | None |
| 44 | 90 | None | 76 | None |
| 45 | 91 | None | 86 | None |
| 46 | 93 | None | 90 | None |
| 53 | 80 | None | 60 | None |
| 54 | 80 | None | 78 | None |
| Probenazole* | 67 | None | 54 | None |
| Untreated | 0 | — | 0 | — |

*Control compound

TEST 3 (Antifungal Activity Against Pyricularia oryzae)

In each test, a colony disk (6 mm in diameter) of Pyricularia oryzae was inoculated to PDA medium which contained 100 ppm of the compound. After the medium was incubated at 25° C. for 5 days, the degree of hyphal growth was investigated. The results are summarized in Table 4.

TABLE 4

| Compound No. | Hyphal growth inhibition rate (%) |
| --- | --- |
| 1 | 0 |
| 2 | 0 |
| 3 | 0 |
| 4 | 0 |
| 5 | 0 |
| 6 | 0 |
| 7 | 0 |
| 8 | 0 |
| 9 | 0 |
| 10 | 0 |
| 19 | 0 |
| 20 | 25 |
| 21 | 31 |
| 22 | 29 |
| 23 | 40 |
| 24 | 35 |
| 25 | 15 |
| 26 | 10 |
| 27 | 10 |
| 28 | 10 |
| 29 | 35 |
| 30 | 35 |
| 31 | 31 |
| 32 | 31 |
| 33 | 0 |
| 34 | 0 |
| 35 | 0 |
| 36 | 0 |

From the results of Tests 1, 2 and 3, it is observed that these isothiazole derivatives showed no significant antifungal activities against *Pyricularia oryzae* but exhibited higher control effects on *Pyricularia oryzae* compared to probenazole, control fungicide, in the pot test in which rice plants were actually used. They are hence effective for the control of *Pyricularia oryzae* in rice cultivation.

Although the invention has been described with preferred embodiments, it is to be understood that variations and modifications may be resorted to as will be apparent to those skilled in the art. Such variations and modifications are to be considered within the purview and the scope of the claims appended hereto.

What is claimed is:

1. An isothiazolecarboxylic acid amide derivative represented by the following formula:

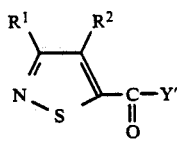

wherein $R^1$ is a methyl group or chlorine atom, $R^2$ is a hydrogen atom or chlorine atom and $Y'$ is $NHR^4$ in which $R^4$ is a linear or branched $C_{6-10}$ alkyl group.

2. An isothiazolecarboxylic acid amide derivative of claim 1, wherein $R^1$ is a methyl group.

3. An isothiazolecarboxylic acid amide derivative of claim 1, wherein $R^1$ is a methyl group and $R^2$ is a hydrogen atom.

4. A rice blast control agent comprising a carrier and, as an active ingredient, an isothiazolecarboxylic acid amide derivative of claim 1.

5. A method of controlling rice blast, comprising applying to rice plants or a field of rice plants an isothiazolecarboxylic acid amide derivative represented by the following formula (II):

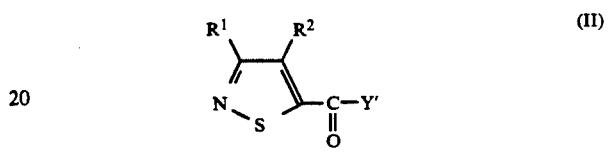

wherein $R^1$ is a hydrogen or halogen atom or a $C_{1-4}$ alkyl or $C_{1-3}$ alkoxyl group, $R^2$ is a hydrogen or halogen atom or a nitro or $C_{1-4}$ alky group, $Y'$ is a morpholino group or an $NHR^4$ group, and $R^4$ is a linear or branched $C_{4-16}$ alkyl, $C_{5-7}$ cycloalkyl, cyclohexenyl, dimethylamino or furfuryl group, or a $C_{1-4}$ alkyl group substituted by one or more $C_{1-8}$ alkoxyl, $C_{1-3}$ alkylthio, phenyl and/or halogenophenyl groups.

6. A method of controlling rice blast, which comprises applying the isothiazolecarboxylic-acid-derivative-containing rice blast control agent of claim 4 to rice plants or a field of rice plants.

7. A method of controlling rice blast, which comprises applying the isothiazolecarboxylic-acid-containing rice blast control agent of claim 4 to rice seedlings before transplanting, at a rate of 4–40 g a.i. per 10 ares.

8. A method of controlling rice blast, which comprises applying the isothiazolecarboxylic-acid-containing rice blast control agent of claim 4 at a rate of 25–250 g per 10 ares.

9. A method of controlling rice blast according to claim 5, which comprises applying the isothazolecarboxylic acid amide derivative to rice seedlings before transplanting, at a rate of 4–10 g a.i. per 10 ares.

10. A method of controlling rice blast according to claim 5, which comprises applying the isothiazolecarboxylic acid amide derivative at a rate of 25–250 g per 10 ares.

* * * * *